United States Patent [19]

Yanagisawa

[11] Patent Number: 4,973,437

[45] Date of Patent: Nov. 27, 1990

[54] METHOD FOR INSPECTING QUALITY OF MODIFIERS OF VINYL CHLORIDE TYPE RESINS

[75] Inventor: Takezi Yanagisawa, Hazaki, Japan

[73] Assignee: Shin-Etsu Chemical Co., Ltd., Japan

[21] Appl. No.: 371,805

[22] Filed: Jun. 27, 1989

[30] Foreign Application Priority Data

Jul. 1, 1988 [JP] Japan ................................ 63-164378

[51] Int. Cl.$^5$ ........................ B29C 43/24; B29C 43/58
[52] U.S. Cl. .................................... 264/40.1; 264/175;
524/495; 524/567; 524/569; 525/76; 525/80;
525/85; 525/197; 525/214; 525/227
[58] Field of Search ...................... 264/40.1, 175, 349;
425/135; 73/159, 866; 524/297, 495, 567, 569;
525/76, 80, 85, 197, 213, 214, 227, 302

[56] References Cited

U.S. PATENT DOCUMENTS

| | | | |
|---|---|---|---|
| 3,903,198 | 9/1975 | Wei | 525/80 |
| 3,983,186 | 9/1976 | Eilers et al. | 525/80 |
| 3,991,135 | 11/1976 | Kraft et al. | 525/85 |
| 4,442,054 | 4/1984 | Dane et al. | 264/40.1 |
| 4,756,855 | 7/1988 | Mathis et al. | 264/22 |

FOREIGN PATENT DOCUMENTS

61-40540 9/1986 Japan.

*Primary Examiner*—Jeffery Thurlow
*Assistant Examiner*—Leo B. Tentoni
*Attorney, Agent, or Firm*—Arnold, White & Durkee

[57] ABSTRACT

A method for inspecting the quality of modifiers for vinyl chloride type resins which includes kneading, with rolls, a soft vinyl chloride resin composition which is free of modifiers and is composed of a stabilizer, a plasticizer and a light shielding pigment to melt the composition and completely remove fish eyes present in the composition; adding a modifier for vinyl chloride type resins to the melted soft vinyl chloride resin composition; again kneading the mixture and then forming the mixture into a sheet to detect and count the number of fish eyes present in the sheet. This method makes it possible to simply and correctly determine the number of fish eyes of modifiers utilizing a widely used apparatus to thereby perform quality inspection of the modifiers. Moreover, when modifiers for vinyl chloride type resins are used in extrusion molding, the method is particularly effective for inspecting the quality of such modifiers.

16 Claims, No Drawings

METHOD FOR INSPECTING QUALITY OF MODIFIERS OF VINYL CHLORIDE TYPE RESINS

BACKGROUND OF THE INVENTION

The present invention relates to a method for inspecting the quality of a modifier for vinyl chloride type resins and, more particularly, to a method for inspecting the quality of a modifier for vinyl chloride type resins which makes it possible to correctly and simply determine the number of fish eyes utilizing widely used apparatuses to perform quality inspection, which is particularly effective when such a modifier for vinyl chloride type resins is used in extrusion molding.

Vinyl chloride type resins are widely used and can be prepared at a low cost. Films, sheets or other various molded products thereof are excellent in a variety of properties such as transparency, resistance to oxygen permeation and printability and, thereof, they have been used as a container or packaging materials as well as vinyl films for agricultural purposes in large quantities.

One of conditions required for the films or sheets thus consumed in large quantities to be satisfied in order that they might be evaluated to have high quality and high commercial value is that they should have a number of fish eyes as low as possible. In most of cases, films and sheets having a lot of fish eyes frequently have so many fatal defects that these are not acceptable as articles of trade since they show a variety of drawbacks due to such defects. For instance, they not only have poor appearance and hence low commercial value but also are inferior in physical properties, and they cause tearing or cracking during fabrication thereof in the form of films and sheets such as vacuum molding and stretching treatment whereby the yield of final products is greatly reduced.

The inventors of the present invention have investigated the causes of the foregoing defects by inspecting and analyzing fish eyes and have found that in products having a lot of fish eyes, there are observed a large amount of non-gelled substances of those added as modifiers such as impact strength modifier (e.g., butadiene-styrene-methyl methacrylate resin (MBS resin)) and acrylic processing aids in addition to contaminants such as fibers and dusts, contaminants which are burnt due to thermal processings and non-gelled vinyl chloride resin as a starting material or the like.

In general, various modifiers such as the aforementioned impact strength modifiers and the processing aids are incorporated into rigid and semi-rigid films and sheets of vinyl chloride resin. In particular, it is almost inevitable to widely use these modifiers in films and sheets produced by blow molding, rigid calendering and T-die extrusion techniques. The amount thereof added to the vinyl chloride resin varies depending on required properties of the final products, but generally it ranges from 5 to 15 parts by weight per 100 parts by weight of vinyl chloride resin (hereinafter referred to as "PHR") for MBS resins, and 0.5 to 5 PHR for acrylic processing aids. The probability of causing fish eyes becomes correspondingly high.

To deal with this problem, as a part of quality control of starting resins, it is necessary to previously perform the quality inspection on the resins. Regarding the vinyl chloride resins, the method for inspecting quality disclosed in Japanese Patent Publication No. 61-40540 by the present applicant or the like may be used. On the other hand, the problem of contamination with foreign substances can be solved, for instance, by the preparation of good environment in manufacturing processes or by improving manners of preventing contamination through the use of bags, clothes and gloves. However, to date, there have not yet been developed any efficient, simple and correct methods for inspecting the quality of added resins such as impact strength modifiers and processing aids.

For instance, as a means for detecting or inspecting fish eyes which have generally been adopted presently, there has been known a method comprising extruding a vinyl chloride type resin compound as a T-die or inflation film utilizing a small-sized extruder provided with a screw having a diameter of 20 to 65 mm and determining the number of fish eyes present in the extruded film. In this case, much time and a lot of analyzing apparatuses are required to correctly investigate the cause of the generation of fish eyes. More specifically, in this method, fish eyes formed due to contaminants may approximately be distinguished from others with a loupe having a magnification of ×50. However, regarding transparent particles or colored but transparent particles, it is required to first carry out chlorine analysis of the particles by an X-ray microanalyzer to thus determine whether these particles are formed due to vinyl chloride resins or not. Then, the particle is treated with osmium oxide and is subjected to analysis with a conventional electron microscope or an X-ray microanalyzer to confirm whether the particle is an MBS resin or not. On the other hand, processing aids have in general qualitatively been analyzed by a combustion gas chromatography technique. In the inspection of fish eyes in accordance with such a method, correct judgment can be achieved only when at least 20 to 30 fish eyes are examined.

SUMMARY OF THE INVENTION

Accordingly, it is an object of the present invention to provide a method for inspecting quality of a modifier for vinyl chloride type resins which can eliminate the foregoing drawbacks of the conventional methods.

Another object of the present invention is to provide a method for inspecting quality of a modifier for vinyl chloride type resins which makes it possible to correctly and simply determine the number of fish eyes using widely used apparatuses to perform quality inspection and which is particularly effective when such a modifier for vinyl chloride type resins is used in extrusion molding.

Other objects of the present invention will be apparent from the description given below.

The inventors of this invention have conducted various studies to achieve the aforementioned objects, have found that these objects can effectively be achieved by determining the number of fish eyes after dispersing a modifier under a relatively low shearing force and after elapsing a desired time period and have completed the present invention on the basis of such a finding.

The method for inspecting quality of modifiers for vinyl chloride resins according to the invention thus comprises adding a modifier to a vinyl chloride type resin composition which has been kneaded and melted to completely remove fish eyes therefrom and which preferably contains a stabilizer, a plasticizer and a light shielding pigment and is free of modifiers, further kneading the mixture and then withdrawing the mixture in the form of sheet to thus detect and count the number of fish eyes present in the sheet.

DETAILED EXPLANATION OF THE INVENTION

The method of this invention will hereunder be explained in more detail.

The method of inspecting quality of modifiers according to the present invention is performed in accordance with the following procedures:

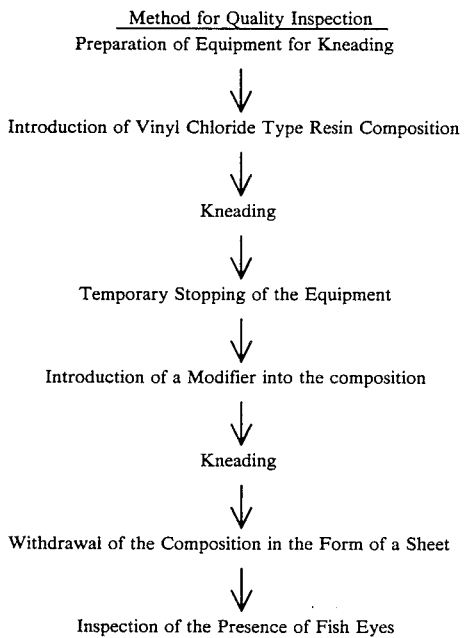

Method for Quality Inspection
Preparation of Equipment for Kneading
↓
Introduction of Vinyl Chloride Type Resin Composition
↓
Kneading
↓
Temporary Stopping of the Equipment
↓
Introduction of a Modifier into the composition
↓
Kneading
↓
Withdrawal of the Composition in the Form of a Sheet
↓
Inspection of the Presence of Fish Eyes It is of primary importance in the present invention to disperse a modifier in a vinyl chloride type resin composition under a relatively low shearing force and to inspect the dispersion state as a function of the number of fish eyes present therein after the lapse of a desired time period to thus investigate the quality of the modifier. The kneading equipments used for this dispersion may be those of any types. For instance, the quality inspection may be performed by correctly and simply determining the number of fish eyes utilizing a widely used test rolling machine.

At this stage, it is preferred that the vinyl chloride type resin composition serving as a base be a soft blend in order to achieve a relatively small shearing force.

Referring now to the soft blend, if dioctyl phthalate (DOP) is used as a plasticizer and the amount thereof added is less than 50 parts by weight per 100 parts by weight of vinyl chloride resin, the melt viscosity of the blend becomes high and fish eyes prematurely disappear when MBS is added to the blend. On the other hand, if the amount of the plasticizer exceeds 90 PHR, the sheet to be inspected becomes too soft to easily handle the same. Therefore, the amount of the plasticizer preferably ranges from 50 to 90 PHR and particularly 75 to 85 PHR.

The vinyl chloride type resins used in the method of this invention are homopolymer preferably having an average degree of polymerization ranging from 1,000 to 1,500. Such a vinyl chloride resin has a proper and moderate melt viscosity, provides a sheet material having good surface quality and can easily be handled when the aforementioned plasticizer is added in an amount ranging from 50 to 90 PHR. If the average degree of polymerization thereof is less than 1,000, the blend of the resin with such a plasticizer becomes too soft to easily handle it even if the plasticizer is used within the range defined above. On the other hand, if the average degree of polymerization exceeds 1,500, not only does the melt viscosity of the resultant blend becomes extremely high but the rate of disappearance of fish eyes becomes too high to determine the number of fish eyes correctly.

In order to facilitate the determination of fish eyes, the resin composition preferably comprises 0.3 to 1.0 part by weight of a light shielding pigment per 100 parts by weight of the vinyl chloride resin. In such cases, it is desirable to use a combination of 0.05 to 0.2 PHR of white pigments and 0.25 to 0.8 PHR, more preferably 0.2 to 0.8, of black pigments.

The resin composition may further comprise a stabilizer which may be any of known ones and is not restricted to a specific one, but preferably they are liquid stabilizers having good dispersibility. The amount thereof used is preferably in the range of from 0.5 to 2.0 PHR per 100 PHR of the vinyl chloride resin.

Examples of the equipment used for kneading these resin compositions are preferably widely used rolling machines, in particular, those provided with rolls having a diameter of 6 to 8 inches and hard chromium plated surfaces and into which a dielectric heating system is desirably incorporated.

The temperature of the roll preferably ranges from 130° to 150° C., more preferably 140°±0.5° C. This is because if it is less than 130° C., fish eyes of the vinyl chloride resin composition serving as a base are hard to remove. Moreover, it is convenient to control the clearance between the rolls for kneading to 0.25 to 0.5 mm so that the thickness of a sheet is equal to 0.3 mm when it is withdrawn from the rolls.

Modifiers to which the method of the present invention is applied include, for instance, impact strength-enhancing agents such as butadiene-styreneacrylonitrile resin (ABS resin), heat resistance-enhancing agents such as chlorinated polyethylene, acrylic processing aids such as methyl methacrylate resin in addition to the aforementioned MBS resin. The addition of these additives is in general carried out after temporarily stopping the rolls about 4 minutes after the initiation of kneading (first kneading) of the vinyl chloride resin composition as the base. The amount of these additives to be added to the resin composition is suitably around 3 PHR. In addition, kneading (second kneading) time after the addition of the additives is preferably about 2 minutes.

The sheets thus obtained are gray colored and opaque all over the sheet while only fish eyes due to the resin as the modifier are transparent. These fish eyes can be observed with an apparatus for determining the number of fish eyes whereby the determination thereof becomes very easy The method for inspecting quality of modifiers for vinyl chloride type resins according to the present invention will hereunder be described in more detail with reference to the following Examples, but the present invention is not restricted to these specific Examples. In addition, the effects practically achieved by the present invention will also be discussed in detail in comparison with the following Comparative Examples.

EXAMPLE 1

A compound of a soft vinyl chloride resin composition having the following composition was prepared.

| Component | Amount (part by weight) |
|---|---|
| Vinyl chloride resin TK-1300 (average degree of polymerization = 1350; available from Shin-Etsu Chemical Co., Ltd.) | 100 |
| Plasticizer DOP | 80 |
| Barium-zinc type stabilizer AC-186 (available from Adeka-Argas Chemical Co., Ltd.) | 1 |
| Epoxy soyabean oil O-130P (available from Adeka-Argas Chemical Co., Ltd.) | 5 |
| Carbon black type pigment C-8728 (available from DAINICHISEIKA COLOR AND CHEMICALS MFG. CO., LTD.) | 0.1 |
| White pigment DAP 4050 (available from DAINICHISEIKA COLOR AND CHEMICALS MFG. CO., LTD.) | 0.5 |

30 g of the resultant compound was kneaded for 4 minutes with rolls having a diameter of 6 inches and a clearance therebetween of 0.3 mm, of which surface temperature was 140° C. and in which the ratio of the rotational speed of the front roll to that of the rear roll was 1.1, thereby completely removing fish eye present in the compound. Thereafter, the rolls were stopped and 1 g of MBS resin was incorporated into the compound, uniformly distributing the MBS resin on the kneaded sheet. The rolls were again rotated and simultaneously the sheet was drawn up to the center of the roll for 5 seconds. The sheet was tented for 5 seconds at its right and left sides, respectively, every 15 seconds from the beginning of the rolling. The way how fish eyes having a diameter of not less than 0.1 mm were disappeared (unit: number/50 $cm^2$; average of five measurements) was observed on MBS resins each having the corresponding grade defined below and the results obtained were summarized in Table I given below.

TABLE I

| Kneading Time (minutes) | 1.5 | 2 | 3 |
|---|---|---|---|
| Grade 1 (product of Company A) | 340 | 205 | 27 |
| Grade 2 (product of Company A) | 360 | 250 | 29 |

As seen from the results listed in Table I, the optimum kneading time was found to be 2 minutes even if the scattering of measurements was taken into consideration.

COMPARATIVE EXAMPLE 1

The same procedures as in Example 1 were repeated except that 40 parts by weight of the plasticizer DOP was substituted for 80 parts by weight thereof and likewise the way the fish eyes having a diameter of not less than 0.1 mm disappeared was determined on MBS resins. The results observed are summarized in the following Table II.

TABLE II

| Kneading Time (minutes) | 1.5 | 2 | 3 |
|---|---|---|---|
| Grade 1 (product of Company A) | 22 | 5 | 2 |
| Grade 2 (product of Company B) | 24 | 6 | 2 |

As seen from the results listed in Table II, there was not observed any significant difference between the results on the products of grade 1 and grade 2. This result indicates that the limitation of the amount of the plasticizer is very important to carry out correct quality inspection.

EXAMPLE 2

Using the same compound as that used in Example 1, each MBS resin having the following grade was added thereto according to the same manner as in Example 1 and the number of fish eyes having a diameter of not less than 0.1 mm observed after kneading for 2 minutes was determined. Moreover, each product having a corresponding grade was extruded through a large-scale extruder as a T-die film of 0.1 mm thick and fish eyes (unit: number/$m^2$) having a diameter of not less than 0.2 mm present in the film were determined. The results thus obtained are listed in the following Table III.

TABLE III

|  | Kneading for 2 min (number/50 $cm^2$) | T-die film (number/$m^2$) |
|---|---|---|
| Grade 1 (product of Company A) | 205 | 15 |
| Grade 3 (product of Company A) | 115 | 8 |
| Grade 4 (product of Company A) | 45 | 5 |
| Grade 5 (product of Company A) | 18 | 3 |

The results listed in Table III indicate that there is a clear correlation between these two methods for determining the number of fish eyes.

EXAMPLE 3

According to the same manner as in Example 1, the number of fish eyes observed after kneading for 2 minutes were determined on acrylic processing aids each having corresponding the grade defined above and the results obtained are summarized in Table IV given below.

TABLE IV

|  | Kneading for 2 minutes (average of 5 measurements) |
|---|---|
| Grade 10 (product of Company A) | 125 number/50 $cm^2$ |
| Grade 11 (product of Company A) | 0 number/50 $cm^2$ |
| Grade 13 (product of Company B) | 105 number/50 $cm^2$ |

As explained above in detail, the method of the present invention makes it possible to simply and correctly determine the number of fish eyes of modifiers utilizing a widely used apparatus to thereby perform quality inspection of the modifiers. Moreover, when modifiers for vinyl chloride type resins, which are subjects of method of this invention, are used in extrusion molding, the method according to this invention is particularly effective for inspecting the quality of such modifiers.

What is claimed is:

1. A method of inspecting the quality of modifiers for vinyl chloride type resins comprising the steps of first kneading a modifier-free, vinyl chloride type resin to remove fish eyes therefrom, adding a modifier to the modifier-free resin, second kneading the resin having said modifier added thereto to form a sheet, and detecting and counting a number of fish eyes in the sheet.

2. The method of claim 1, wherein the modifier-free resin has an average degree of polymerization ranging from 1,000 to 1,500.

3. The method of claim 1, wherein the modifier-free resin and the resin having said modifier added thereto in the first and second kneading steps, respectively, are kneaded using rolls.

4. The method of claim 3, wherein said rolls are heated at a temperature ranging from 130° to 150° C. in the first and second kneading steps.

5. The method of claim 3, wherein each of said rolls is maintained at a clearance ranging from 0.25 to 0.5 mm in the first and second kneading steps.

6. The method of claim 1, wherein the modifier-free resin comprises a stabilizer, a plasticizer and a light shielding pigment.

7. The method of claim 6, wherein an amount of said plasticizer used in the modifier-free resin ranges from 50 to 90 parts by weight per 100 parts by weight of the modifier-free resin.

8. The method of claim 6, wherein said light shielding pigment comprises 0.05 to 0.2 parts by weight of a white pigment and 0.2 0.8 parts by weight of a black pigment per 100 parts by weight of the modifier-free resin.

9. The method of claim 8, wherein an amount of said black pigment in said light shielding pigment ranges from 0.25 to 0.8 parts by weight per 100 parts by weight of the modifier-free resin.

10. The method of claim 6, wherein an amount of said light shielding pigment used in the modifier-free resin ranges from 0.3 to 1.0 parts by weight per 100 parts by weight of the modifier-free resin.

11. The method of claim 10, wherein said light shielding pigment comprises 0.05 to 0.2 parts by weight of a white pigment and 0.2 to 0.8 parts by weight of a black pigment per 100 parts by weight of the modifier-free resin.

12. The method of claim 11, wherein an amount of said black pigment in said light shielding pigment ranges from 0.25 to 0.8 parts by weight per 100 parts by weight of the modifier-free resin.

13. The method of claim 1, wherein said modifier is selected from the group consisting of an impact strength-enhancing agent, a heat resistance-enhancing agent and an acrylic processing aid.

14. The method of claim 13, wherein said impact strength-enhancing agent consists of butadiene-styrene-acrylonitrile resin.

15. The method of claim 13, wherein said heat resistance-enhancing agent consists of a chlorinated polyethylene resin.

16. The method of claim 13, wherein said acrylic processing aid is selected from the group consisting of a butadiene-styrene-methyl methacrylate resin and a methyl methacrylate resin.

* * * * *